(12) United States Patent
Ferraz De Souza et al.

(10) Patent No.: US 10,370,604 B2
(45) Date of Patent: Aug. 6, 2019

(54) PROCESS FOR SIMULTANEOUS REMOVAL OF ARSENIC AND SULPHUR FROM HYDROCARBON STREAMS

(71) Applicant: PETROLEO BRASILEIRO S.A.—PETROBRAS, Rio de Janeiro (BR)

(72) Inventors: Wladmir Ferraz De Souza, Rio de Janeiro (BR); Marcus Vinicius Eiffle Duarte, Niterói (BR); Lilian Ernst, São Mateus do Sul (BR); Carmen Lucia Tavares Da Silva, Rio de Janeiro (BR)

(73) Assignee: PETROLEO BRASILEIRO S.A.—PETROBRAS, Rio de Janeiro (BR)

(*) Notice: Subject to any disclaimer, the term of this patent is extended or adjusted under 35 U.S.C. 154(b) by 0 days.

(21) Appl. No.: 15/717,009

(22) Filed: Sep. 27, 2017

(65) Prior Publication Data

US 2018/0086992 A1    Mar. 29, 2018

(30) Foreign Application Priority Data

Sep. 29, 2016 (BR) .................. 10 2016 022626

(51) Int. Cl.
| | |
|---|---|
| *B01D 53/48* | (2006.01) |
| *C10G 49/02* | (2006.01) |
| *C10G 70/04* | (2006.01) |
| *B01J 20/02* | (2006.01) |
| *B01J 20/30* | (2006.01) |
| *C01G 49/02* | (2006.01) |
| *C07C 7/148* | (2006.01) |
| *C10G 25/00* | (2006.01) |
| *C10G 31/06* | (2006.01) |
| *B01D 53/64* | (2006.01) |

(52) U.S. Cl.
CPC .......... *C10G 70/046* (2013.01); *B01D 53/48* (2013.01); *B01D 53/64* (2013.01); *B01J 20/0229* (2013.01); *B01J 20/3028* (2013.01); *B01J 20/3078* (2013.01); *C01G 49/02* (2013.01); *C07C 7/1485* (2013.01); *C10G 25/003* (2013.01); *C10G 31/06* (2013.01); *B01D 2253/1124* (2013.01); *B01D 2256/24* (2013.01); *B01D 2257/306* (2013.01); *B01D 2257/60* (2013.01); *B01J 2220/42* (2013.01); *C10G 2300/202* (2013.01)

(58) Field of Classification Search
None
See application file for complete search history.

(56) References Cited

U.S. PATENT DOCUMENTS

| | | |
|---|---|---|
| 3,876,533 A | 4/1975 | Myers |
| 6,544,409 B2 | 4/2003 | De Souza |
| 2002/0189975 A1 | 12/2002 | De Souza |

*Primary Examiner* — Tam M Nguyen
(74) *Attorney, Agent, or Firm* — Sughrue Mion, PLLC

(57) ABSTRACT

The present invention describes a process for the simultaneous removal of arsenic and sulphur compounds from hydrocarbon streams of fossil origin, wherein hydrocarbon streams of fossil origin resulting from the retorting process of schist are purified by direct contact with hydrated iron oxide, such as goethite (α-FeOOH) in its raw natural form (limonite ore particles).

14 Claims, 1 Drawing Sheet

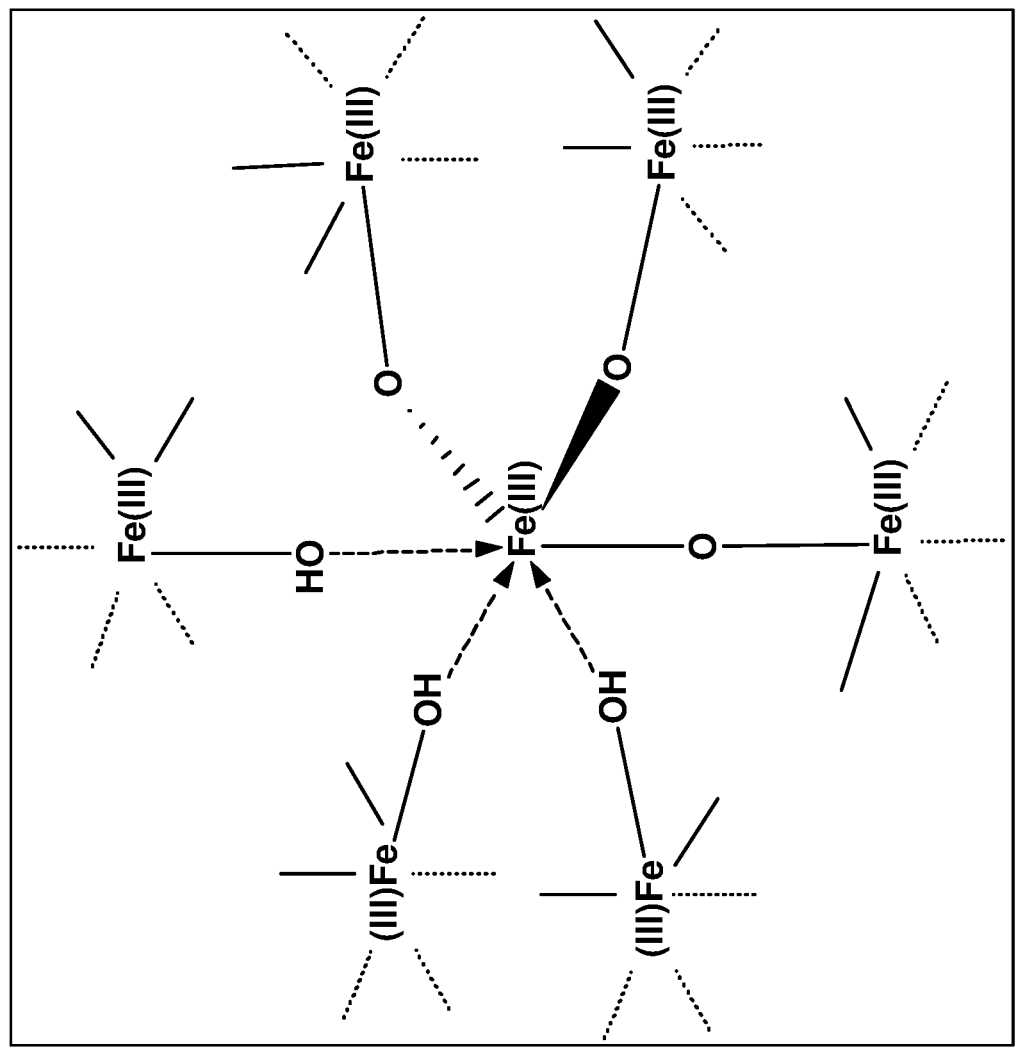

PROCESS FOR SIMULTANEOUS REMOVAL OF ARSENIC AND SULPHUR FROM HYDROCARBON STREAMS

CROSS-REFERENCE TO RELATED APPLICATION

This application claims the benefit of priority to BR 10 2016 022626-0, filed Sep. 29, 2016, which is incorporated herein by reference in its entirety.

FIELD OF THE INVENTION

The present invention relates to a process suitable for the simultaneous removal of arsenic and sulphur compounds from hydrocarbon streams of fossil origin. More specifically, the present invention proposes the purification of hydrocarbon streams of fossil origin resulting from the retorting process of schist by direct contact with hydrated ferric oxide, such as goethite ($\alpha$-FeOOH) in its natural raw form (particles of the ore limonite).

BACKGROUND OF THE INVENTION

A problem encountered during the treatment of certain hydrocarbon streams of fossil origin is contamination due to the presence of arsenic compounds and sulphur. Besides the resultant toxicological and environmental impacts, these compounds also act as poisons for catalysts of chemical processes, and may affect the catalyst by both physical and chemical adsorption. The presence of these compounds in hydrocarbon streams of fossil origin compromises the performance of catalytic processes for treating them, such as the processes of catalytic hydrotreating (HDT) carried out in refineries. HDT catalysts are vulnerable to these compounds, and may undergo considerable deactivation, promoting operational discontinuity and raising the costs of catalyst replacement.

The feedstocks of the refining processes that are subject to contamination with arsenic compounds include the middle and light distillates derived from materials of fossil origin such as petroleum, schist, bituminous sands or coal, more particularly derived from shale oil, which may possibly form part of feeds of refinery units, whose effluents must undergo the processes of catalytic hydrotreating, putting the catalysts of the process at risk.

Shale oil is an oily stream consisting of organic substances, usually extracted from schist rock by means of retorting processes, basically pyrolysis at temperatures of the order of 450-600° C. The shale oil resulting from these processes may have high contents of arsenic, contaminating compounds of which may appear over the whole range of distillation of shale oil. In particular, streams of distillates in the entire naphtha range (40° C.-290° C.), which are processed in refinery treatment units, such as units for catalytic HDT, may contain arsenic compounds, which act as poison of the catalysts in these units, and put their performance and useful life at risk. Therefore it is necessary to remove said arsenic compounds from these streams.

Gaseous hydrocarbon streams may also contain arsenic compounds, such as trivalent arsines and/or pentavalent arsines. In the case of gas streams produced by hydraulic fracturing of schist in subsoils accompanied by acidification employing acids such as HF or HCl, arsenic compounds in the geological formation may then be lixiviated, generating arsenic acids.

At present, there are various alternatives for removal of arsenic from derivatives of hydrocarbon streams, including shale oil. The commonest processes include processes of removal by coking of schist rock followed by washing with water or with caustic solution, as well as catalytic removal in the presence of pressurized $H_2$, employing guard beds containing spent hydrotreating catalysts based on nickel or cobalt or molybdenum supported on alumina or sulphided silica. The arsenic compounds contained in the gas streams can be removed by pyrolysis processes, where they are collected as metallic arsenic, by adsorption on solids such as zinc oxide or copper oxide, or may also be removed by extraction processes, using an oxidizing solution such as potassium permanganate solution or using organic solvents.

Moreover, processes for catalytic removal are described that employ materials based on oxides or sulphides of iron, nickel or cobalt in the presence of hydrogen at high pressure (of the order of 1500 psig or 10.34 MPa) in guard beds or sludge beds. Arsenic oxides ($As_2O_3$) can be removed from gaseous hydrocarbon streams by adsorption on iron oxides at high temperatures (>600° C.) using fixed beds consisting of microparticles of $Fe_2O_3$ or CaO or $Al_2O_3$. In ambient conditions, iron oxides and hydrated iron oxides have been reported with dearsenization agents of aqueous media, for water purification.

Systems for adsorption of As compounds from aqueous media using iron oxides as adsorbent have been investigated and are well known. Possible materials are $Fe_2O_3$, whether hydrated or not, $Fe(OH)_3$, FeOOH, limonite or laterites.

In this connection, the document Wainipee, W, "*The effect of crude oil on arsenate adsorption on goethite*", (Univ London Imperial Coll Sci Technol & Med) WATER RESEARCH, 44 (19): 5673-5683 Sp. Iss. SI November 2010, discloses a study on the adsorption of arsenate (As(V)) on the surface of synthetic goethite ($\alpha$-FeOOH) and of goethite coated with oil in conditions that simulate the conditions of oil field wastewater (aqueous solution containing $Na^+HAsO_4^-$, at a temperature of 25° C. and with controlled NaCl concentration and pH). This document discloses that, in both cases, adsorption is rapid, but without appreciable removal of arsenic. It was demonstrated that the mechanism of adsorption is described better with the Langmuir model, as the capacity for adsorption increases with decrease in pH, which reflects the increase in positive charges on the surface of goethite. Furthermore, the FTIR results show that As(V) interacts with the carbonyl functional groups of the oil and is removed exclusively in the form of inorganic arsenide ions ($HAsO_4$) present in wastewater from petroleum production, mainly offshore production, which must be treated before being discharged back into the natural environment around the platform.

Moreover, document U.S. Pat. No. 3,876,533 deals with a method for removing impurities or contaminants that poison catalysts, such as arsenic and selenium, from hydrocarbon fluids, such as crude synthetic oil and synthetic oil fractions, by hydrogenation under partial pressure of at least 1500 psi on the surface of particles of $Fe_2O_3$, $Fe_3O_4$, $Ni_2O_4$, $Ni_3O_4$, $Co_2O_3$, $Co_3O_4$ or their respective sulphides, without the need to use aqueous or hydrophilic solutions. This document shows that a stream of shale oil containing about 80 ppm of As is mixed with hydrogen and then is passed through a fixed bed containing particles of $Fe_2O_3$ in extruded pellets of cylindrical shape, at a temperature of 371° C. and a pressure of about 100 bar. The residence time is sufficient to allow the contaminant to be removed from the oil and deposited on at least the surface layer of the particles of material, giving 87.5% reduction in total As content.

The document Viet, P H, et al., "*Investigation of arsenic removal technologies for drinking water in Vietnam*", ARSENIC EXPOSURE AND HEALTH EFFECTS V (2003) 459-469 deals with a method for reducing the concentrations of As(III) and As(V) in the form of dissociated ions ($AsO_3^{3-}$ and $AsO_4^{3-}$) dissolved in potable water. As shown in the results of sorption experiments, the co-precipitation of arsenate [As(V)] on ferric hydroxide is much more efficient than that of arsenite [As(III)], it being possible to reduce the content of As(V) by more than 90%. In this study, so that they could be used as adsorbent, limonite and laterite were treated by alkaline washing and heating at 900° C., converting crystalline phases of FeOOH to $Fe_2O_3$, which has potential as adsorbent of anionic arsenic species.

Finally, document U.S. Pat. No. 6,544,409 deals with a process for the simultaneous removal of sulphur, nitrogen and unsaturated compounds aided by the catalytic action of limonite clays in the presence of a peracid. In this process there is extractive oxidation of unstable sulphurized, nitrogenated and unsaturated compounds by an aqueous solution containing RCOOH, $H_2O_2$ and natural goethite (limonite), which acts as a catalyst, permitting the generation of oxidizing free radicals in mild conditions (atmospheric pressure and maximum temperature of approximately 80° C.). The process makes use of the dispersive character of pulverized limonite ore in oil so as to perform direct Fenton-type oxidation of sulphur and nitrogen present in an oil phase, it being especially suitable for the removal of sulphur, nitrogen and unsaturated compounds from light, middle and heavy distillates obtained from petroleum, liquefied coal, shale oil and tar, preferably heavy diesel oil or gas oils from petroleum.

Thus, it can be seen that there are no reports in the prior art that anticipate a process for removing arsenic and sulphur compounds using natural α-FeOOH (goethite), in the absence of hydrogen and at atmospheric pressure.

SUMMARY OF THE INVENTION

The present disclosure relates to a process for purifying hydrocarbon streams of fossil origin, in conditions in which the arsenic and sulphur compounds are reacted and immobilized, and are removed from said streams.

A first aim is to allow the removal of arsenic compounds in parallel with the removal of sulphurized compounds from hydrocarbon streams of fossil origin contaminated with these compounds, such as, for example: hydrocarbon streams resulting from the industrial retorting process of schist rock, gaseous streams of light hydrocarbons and streams of gaseous or liquid hydrocarbons derived from petroleum or from coal.

A second aim is to minimize the number of subsequent steps of purification of these streams, also promoting an increase in the useful life of catalysts in subsequent steps, for example catalysts of HDT units, which may be contaminated with arsenic and sulphur compounds.

In order to achieve the aims described above, the present disclosure proposes a process for simultaneous removal of arsenic and sulphur from hydrocarbon streams, comprising the steps of
  a) grinding schist rock to obtain particles of schist rock;
  b) mixing the particles of schist rock with particles of hydrated iron oxide (FeOOH) in a schist:FeOOH ratio, by weight, in the range from 100:1 to 1:100; and
  c) pyrolysis of the mixture a)+b) with heating from ambient temperature to a temperature in the range 400-600° C., simulating retorting conditions,
wherein the process takes place in the absence of hydrogen partial pressure and at atmospheric pressure.

A further aspect of the disclosure provides that particles of schist rock are ground to a granulometry in the range between 3.5 and 20 Tyler mesh (between 5.6 and 0.85 mm), preferably 6 Tyler mesh (3.6 mm).

A further aspect of the disclosure provides that particles of schist rock are mixed with particles of FeOOH in a schist:FeOOH ratio, by weight, in the range from 1:1 to 50:1.

A further aspect of the disclosure provides that the particles of hydrated iron oxide (FeOOH) are particles of goethite (α-FeOOH) in the natural form of limonite ore.

A further aspect of the disclosure provides that pyrolysis of the mixture a)+b) is carried out with heating from ambient temperature to a temperature of 500° C., simulating retorting conditions.

A further aspect of the disclosure provides that the arsenic compounds that are removed are selected from the group consisting of organic compounds of As(III) and As(V), including arsines ($R_3As$), oxides of arsenic ($R_3As=O$, $RAs=O$, $R_2AsOH$) and organic arsenides ($O=AsR(OH)_2$, $O=AsR_2(OH)$).

A further aspect of the disclosure provides that the sulphur compounds that are removed are mercaptides.

Also proposed is a process for simultaneous removal of arsenic and sulphur from hydrocarbon streams, comprising the steps of
  a) extruding paste of limonite ore particles, followed by drying; and
  b) passing a hydrocarbon stream contaminated with arsenic and sulphur through the bed obtained in a) at a temperature of at least 80° C., varying up to 420° C.,
wherein the process takes place in the absence of hydrogen partial pressure and at atmospheric pressure.

A further aspect of the disclosure provides that extrusion of particles of natural limonite and drying at 120° C., for 3 hours, are carried out in a $N_2$ stream.

A further aspect of the disclosure provides that the hydrocarbon streams of fossil origin are selected from the group consisting of: hydrocarbon streams resulting from the industrial retorting process of schist rock; gaseous streams of light hydrocarbons; and gaseous or liquid hydrocarbon streams derived from petroleum or from coal.

A further aspect of the disclosure provides that the hydrocarbon stream of fossil origin is a hydrocarbon stream resulting from the industrial retorting process of schist rock and is selected from shale oil and the distilled derivatives thereof.

A further aspect of the disclosure provides that the hydrocarbon stream of fossil origin is a gaseous stream of light hydrocarbons and is shale gas resulting from processes of fracturing in subsoils.

A further aspect of the disclosure provides that the arsenic compounds that are removed are selected from the group consisting of organic compounds of As(III) and As(V), including arsines ($R_3As$), oxides of arsenic ($R_3As=O$, $RAs=O$, $R_2AsOH$) and organic arsenides ($O=AsR(OH)_2$, $O=AsR_2(OH)$).

A further aspect of the disclosure provides that the sulphur compounds that are removed are mercaptides.

The present disclosure proposes direct contact of hydrocarbon streams resulting from the retorting process of schist with hydrated iron oxide, such as goethite (α-FeOOH) in its raw natural form (limonite ore particles), on the surface of which arsenic compounds can be reacted selectively together with sulphur compounds, and optionally are immobilized in another mineral form, such as arsenopyrite or similar.

The present disclosure removes arsenic and sulphur with natural goethite (limonite), reaching levels of removal of these impurities higher than those disclosed in the prior art, minimizing or even eliminating the toxicological risks due to the presence of arsenic compounds, without requiring high pressures and $H_2$, treatment of the limonite and in conditions in which there is no possibility of any aqueous phase existing.

Moreover, the process according to the disclosure makes removal of arsenic possible, allowing a substantial amount of stock to be upgraded, streams from refining of shale and petroleum for treatment in hydrofining units for production of specified fuels, minimizing or eliminating all the negative environmental impacts generated.

The route now proposed applies to the concomitant removal of contaminating compounds of arsenic and sulphur not from aqueous media, but from oily or gaseous organic media, in specific temperature conditions, at atmospheric pressure or at least at atmospheric pressure, and taking place in the presence or in the absence of hydrogen.

In the case when the process is applied for removing arsenic compounds from hydrocarbon streams resulting from the retorting process of schist, the arsenic content in the shale oil resulting from retorting may be reduced by at least 96% w/w when particles of schist rock are mixed directly and homogeneously with particles of natural limonite, ground to the same granulometry and submitted to retorting conditions.

The disclosure further proposes the alternative operating mode where hydrocarbon streams percolate through fixed beds loaded with limonite particles either in the form of pellets or in the form of extrudates, in such a way that the stream flows through the bed in optimized conditions of time and temperature, without entrainment and without collapse of the particles of the bed.

The process according to the present disclosure is innovative in that it allows concomitant removal of at least 98% w/w of sulphurized compounds and removal of at least 98.9% w/w of mercaptans.

These aims and other advantages will become clearer from the description that follows and the appended drawings.

BRIEF DESCRIPTION OF THE FIGURES

The detailed description presented hereunder refers to the appended FIGURE.

FIG. 1 shows the crystalline structure of goethite to be used in the natural form (limonite ore particles) in the proposed process.

DETAILED DESCRIPTION OF THE INVENTION

The present disclosure relates to a process for removing arsenic and sulphur compounds from hydrocarbon streams of fossil origin in the presence or absence of hydrogen and at atmospheric pressure, using particles of hydrated iron oxide (FeOOH). The particles of hydrated iron oxide may be goethite ($\alpha$-FeOOH) or lepidocrocite ($\gamma$-FeOOH) or akaganéite ($\beta$-FeOOH) or feroxyhyte ($\delta$-FeOOH) in their synthetic or natural forms, pure or combined. The particles of hydrated iron oxide are preferably goethite ($\alpha$-FeOOH) in its natural form (limonite).

In the context of the present disclosure, "arsenic compounds" means the arsenic compounds in general, preferably organic compounds of As(III) and As(V), including arsines ($R_3As$), oxides of arsenic ($R_3As\!=\!O$, $RAs\!=\!O$, $R_2AsOH$) and organic arsenides ($O\!=\!AsR(OH)_2$, $O\!=\!AsR_2(OH)$) contaminating gaseous or liquid hydrocarbon streams.

Hydrocarbon streams of fossil origin are to be understood as those selected from the group consisting of: hydrocarbon streams resulting from the industrial retorting process of schist rock, such as gaseous streams and liquid streams such as shale oil and the distilled derivatives thereof, including shale naphtha; gaseous streams of light hydrocarbons such as shale gas resulting from processes of fracturing in subsoils, such as the hydraulic fracturing process, using acidification of the fracturing fluid; gaseous or liquid hydrocarbon streams derived from petroleum or from coal.

The process of the present disclosure proposes, firstly, a process that begins with attractive interaction of the surface of dry natural goethite by the polar compounds of arsenic and sulphurized compounds present in the hydrocarbon medium (gaseous and liquid) until transformation of the surface of $\alpha$-FeOOH (goethite) to a structure such as that of the surface of arsenopyrite, or a similar structure, definitively immobilizing arsenic and sulphur compounds such as occurs, for example, in the reaction:

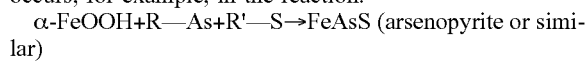

In the present disclosure, limonite may be submitted to a heating ramp from ambient temperature or approximately 80° C. up to about 600° C., preferably between 400 and 580° C., so that from the ambient temperature (or approximately 80° C.) up to about 200° C. there is removal of the surface hydration layers from $\alpha$-FeOOH and attraction of the polar species, whereas from about 200° C. up to approximately 500° C. there is modification of the crystalline structure and reaction of these species.

According to the present disclosure, the process has two aspects:

a) Process A—Mixed bed operating mode: homogeneous mixture of particles of schist with particles of FeOOH, such as goethite ($\alpha$-FeOOH) in the natural form of limonite ore, with subsequent simulation of the retorting process;

b) Process B—Fixed bed operating mode: flow of a hydrocarbon stream through a fixed bed of limonite ore particles (in the form of pellets or extrudates).

In a first embodiment of the process (process A), schist rock is ground to a granulometry in the range between 3.5 and 20 Tyler mesh (between 5.6 and 0.85 mm), preferably 6 Tyler mesh (3.6 mm). and the schist rock is then mixed with limonite ore particles in a schist:limonite ratio, by weight, in the range from 1:1 to 5:1, preferably 4:1. The mixture is then submitted to the Fischer test, where the particles are treated in conditions of pyrolysis, with heating from ambient temperature to a temperature in the range from 400 to 600° C., preferably 500° C., simulating the conditions of retorting.

Briefly, the process according to the first embodiment comprises the steps of a) grinding schist rock to obtain particles of schist rock;
b) mixing the particles of schist rock with particles containing hydrated iron oxide (FeOOH) in a schist:FeOOH ratio, by weight, in the range from 100:1 to 1:100, preferably 1:1 to 50:1, and;
c) pyrolysis of the mixture a)+b) with heating from ambient temperature to a temperature in the range 400-600° C., wherein the process takes place in the absence of hydrogen partial pressure and at atmospheric pressure.

In a second embodiment of the process (Process B), a hydrocarbon stream of fossil origin contaminated with arsenic and sulphur is passed through a bed of extruded particles, consisting of limonite ore. The extruded particles are prepared by extrusion of paste consisting of natural limonite and dilute solution of binder, homogenized and dried to remove all moisture. The naphtha stream was passed at temperatures of at least 80° C., varying up to 420° C., through the bed of dry limonite.

Briefly, the process according to the second embodiment comprises the steps of:
- a) extruding paste of limonite ore particles, followed by drying; and
- b) passing a hydrocarbon stream contaminated with arsenic and sulphur through the bed obtained in a) at a temperature of at least 80° C., varying up to 420° C., wherein the process takes place in the absence of hydrogen partial pressure and at atmospheric pressure.

The description that follows will be based on preferred embodiments of the invention. As will be obvious to a person skilled in the art, the invention is not limited to these particular embodiments.

EXAMPLES

To demonstrate the greater efficiency of the process disclosed here, tests for removal of contaminants were carried out, as described in the following examples:

Example 1: Obtaining Shale Oil

A sample of schist rock obtained from schist mining of São Mateus do Sul, Paraná, Brazil, was ground to a granulometry of 6 Tyler mesh (3.6 mm) and submitted to the Fischer test (ASTM D3904-90). The particles obtained were submitted to the pyrolysis conditions, with heating from ambient temperature (25° C.) to a temperature of 500° C., simulating the retorting process. The test made it possible to collect the shale oil produced in the form of condensate, with a yield of 9% w/w and with a content of 30,300 ppb of total arsenic according to the test by ICP-MS (Inductively coupled plasma mass spectrometry) and content of 1.28% w/w of total sulphur.

Example 2

A sample of schist rock obtained from schist mining of São Mateus do Sul, Paraná, Brazil, was ground to a granulometry of 6 Tyler mesh (3.6 mm). Homogeneous mixing of 80 g of these schist particles with 20 g of limonite ore particles, obtained from nickel mining deposits of Niquelândia, Goiás, Brazil, containing 52% w/w of Fe; and 70-80% of α-FeOOH, was carried out. The mixture was submitted to the Fischer test (ASTM D3904-90), where the particles were treated in conditions of pyrolysis, with heating from ambient temperature (25° C.) to a temperature of 500° C., simulating the retorting conditions, as in example 1. The test made it possible to collect the shale oil, produced in the form of condensate, with a yield of 9% w/w and with a content of 1200 ppb of total arsenic according to the test by ICP-MS (Inductively coupled plasma mass spectrometry) and 0.81% w/w of total sulphur. In this way, the process now proposed gave a reduction of 96.0% w/w of the total arsenic content and removal of 36.7% of the total sulphur content compared to the shale oil obtained from pure schist.

Example 3

A naphtha stream derived from petroleum refining in the distillation range between 20° C. and 196° C., containing 485 ppm of total sulphur, 183 ppm of mercaptide sulphur and 5000 ppb of arsenic was used as contaminated feed to be treated. This naphtha stream was passed through a bed of extruded particles, consisting of limonite ore. The limonite used was obtained from nickel mining deposits of Niquelândia, Goiás, Brazil, containing 52% w/w of Fe; and 70-80% of α-FeOOH. Extruded particles were used to facilitate flow of the naphtha through the bed, avoiding blocking of the flow by any collapse of the limonite particles, which are friable in their natural form. The extruded particles were prepared by extrusion of paste consisting of natural limonite and dilute solution of binder, homogenized and dried for 3 hours to remove all moisture. The fixed bed of particles of extruded limonite was further submitted to drying at 120° C. for 3 hours, in a stream of $N_2$. The naphtha stream was passed through the bed of dry limonite at temperatures of at least 80° C., varying up to 420° C. The resultant treated naphtha stream contained at least 8 ppb of total arsenic (99.8% w/w of removal), at least 8 ppm of total sulphur (98% w/w of removal) and at least 2 ppm of mercaptide sulphur (98.9% w/w of removal), depending on the degree of saturation of the bed, the residence time and the operating temperature.

The description provided up to here of the subject matter of the present invention must be considered only as one possible embodiment or possible embodiments, and any particular features introduced therein must be understood only as something that has been written to facilitate understanding. Modification of the above-described processes, combinations between different variations as practicable, and variations of aspects of the invention that are obvious to those of skill in the art are intended to be within the spirit and scope of the claims.

What is claimed is:
1. A process for simultaneous removal of arsenic and sulphur from hydrocarbon streams, comprising the steps of
   a) grinding schist rock contaminated with arsenic and sulphur to obtain particles of schist rock;
   b) removing the arsenic and sulphur from the particles of schist rock by
      b1) mixing the particles of schist rock with particles of hydrated iron oxide (FeOOH) in a schist:FeOOH ratio, by weight, in the range from 100:1 to 1:100 and
      b2) pyrolyzing the mixture obtained in step b1) with heating from ambient temperature to a temperature in the range 400-600° C.,
   wherein the process takes place in the absence of hydrogen partial pressure and at atmospheric pressure.

2. The process according to claim 1, wherein the particles of schist rock are ground to a granulometry in the range between 3.5 and 20 Tyler mesh.

3. The process according to claim 1, wherein the particles of schist rock are mixed with particles of FeOOH in a schist:FeOOH ratio, by weight, in the range from 1:1 to 50:1.

4. The process according to claim 1, wherein the particles of hydrated iron oxide (FeOOH) are particles of goethite (α-FeOOH) in the natural form of limonite ore.

5. The process according to claim 1, wherein the pyrolyzing step b2) is carried out with heating from ambient temperature to a temperature of 500° C.

6. The process according to claim 1, wherein arsenic compounds selected from the group consisting of organic compounds of As(III) and As(V) are removed.

7. The process according to claim 1, wherein mercaptides are removed.

8. A process for simultaneous removal of arsenic and sulphur from hydrocarbon streams, comprising the steps of
   a) extruding paste of limonite ore particles, followed by drying; and
   b) removing arsenic and sulphur from a hydrocarbon stream contaminated with arsenic and sulphur by passing the hydrocarbon stream through the bed obtained in a) at a temperature of at least 80° C., varying up to 420° C.,
   wherein the process takes place in the absence of hydrogen partial pressure and at atmospheric pressure.

9. The process according to claim 8, wherein extrusion of particles of natural limonite and drying at 120° C., for 3 hours, are carried out in a $N_2$ stream.

10. The process according to claim 8, wherein hydrocarbon streams of fossil origin are treated, selected from the group consisting of: hydrocarbon streams resulting from the industrial retorting process of schist rock; gaseous streams of light hydrocarbons; gaseous or liquid hydrocarbon streams derived from petroleum or from coal.

11. The process according to claim 10, wherein the hydrocarbon stream of fossil origin is a hydrocarbon stream resulting from the industrial retorting process of schist rock and is selected from shale oil and the distilled derivatives thereof.

12. The process according to claim 10, wherein the hydrocarbon stream of fossil origin is a gaseous stream of light hydrocarbons and is shale gas resulting from processes of fracturing in subsoils.

13. The process according to claim 8, wherein arsenic compounds selected from the group consisting of organic compounds of As(III) and As(V) are removed.

14. The process according to claim 8, wherein mercaptides are removed.

* * * * *